US011730708B2

(12) United States Patent
Haksar et al.

(10) Patent No.: US 11,730,708 B2
(45) Date of Patent: Aug. 22, 2023

(54) DOSAGE FORM FOR USE IN TREATING OR PREVENTING OF A DISEASE

(71) Applicant: Evonik Operations GmbH, Essen (DE)

(72) Inventors: Priyanka Haksar, Thane (IN); Shraddha Joshi, Thane (IN); Umesh Kapale, Solapur (IN); Nilam Bharambe, Dombivali West (IN); Ashish Guha, Mumbai (IN); Vinay Jain, Mumbai (IN)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 17/757,043

(22) PCT Filed: Sep. 17, 2020

(86) PCT No.: PCT/EP2020/075962
§ 371 (c)(1),
(2) Date: Jun. 8, 2022

(87) PCT Pub. No.: WO2021/115650
PCT Pub. Date: Jun. 17, 2021

(65) Prior Publication Data
US 2023/0012981 A1   Jan. 19, 2023

(30) Foreign Application Priority Data

Dec. 11, 2019 (IN) .............................. 201941051259

(51) Int. Cl.
| | |
|---|---|
| *A61K 9/50* | (2006.01) |
| *A61K 31/145* | (2006.01) |
| *A61K 9/20* | (2006.01) |
| *A61K 9/28* | (2006.01) |
| *A61K 31/137* | (2006.01) |
| *A61K 31/155* | (2006.01) |
| *A61K 31/404* | (2006.01) |
| *A61K 31/405* | (2006.01) |
| *A61K 31/4402* | (2006.01) |
| *A61K 31/4706* | (2006.01) |
| *A61K 31/496* | (2006.01) |
| *A61K 31/55* | (2006.01) |
| *A61K 31/58* | (2006.01) |
| *A61K 31/635* | (2006.01) |
| *A61K 31/7048* | (2006.01) |

(52) U.S. Cl.
CPC .......... *A61K 31/145* (2013.01); *A61K 9/2054* (2013.01); *A61K 9/2813* (2013.01); *A61K 9/2826* (2013.01); *A61K 9/2846* (2013.01); *A61K 9/2866* (2013.01); *A61K 31/137* (2013.01); *A61K 31/155* (2013.01); *A61K 31/404* (2013.01); *A61K 31/405* (2013.01); *A61K 31/4402* (2013.01); *A61K 31/4706* (2013.01); *A61K 31/496* (2013.01); *A61K 31/55* (2013.01); *A61K 31/58* (2013.01); *A61K 31/635* (2013.01); *A61K 31/7048* (2013.01)

(58) Field of Classification Search
None
See application file for complete search history.

(56) References Cited

U.S. PATENT DOCUMENTS

| | | | |
|---|---|---|---|
| 4,786,505 A | * 11/1988 | Lovgren | .............. A61K 9/2009 424/475 |
| 7,932,258 B2 | 4/2011 | Petereit et al. | |
| 9,237,760 B2 | 1/2016 | Ravishankar et al. | |
| 10,842,752 B2 | 11/2020 | Haksar et al. | |
| 2002/0098232 A1 | 7/2002 | Midha et al. | |
| 2005/0214371 A1 | 9/2005 | Di Capua et al. | |
| 2010/0247639 A1 | 9/2010 | Ravishankar et al. | |
| 2010/0255092 A1 | 10/2010 | Ravishankar et al. | |

(Continued)

FOREIGN PATENT DOCUMENTS

| | | |
|---|---|---|
| CN | 102626398 | 8/2012 |
| EP | 3117824 A1 * | 1/2017 |
| EP | 3388056 | 10/2018 |
| GB | 2189698 | 11/1987 |
| WO | 2005/092297 | 10/2005 |

(Continued)

OTHER PUBLICATIONS

Extended European Search Report dated Jul. 13, 2020 in European Patent Application No. 20153822.0, 8 pages.

(Continued)

*Primary Examiner* — Susan T Tran
(74) *Attorney, Agent, or Firm* — Grüneberg and Myers PLLC

(57) ABSTRACT

A dosage form contains a biologically active ingredient for treating or preventing a disease in the animal or human body, where the treatment or prevention requires release of 50% or more of the biologically active ingredient in the small intestine within the pH range from 3 to 5.5. The dosage form contains: a) a core, containing the biologically active ingredient; b) an intermediate coating layer (ICL) onto or above the core, containing an alkaline agent; and c) an enteric coating layer (ECL) onto or above the intermediate coating layer, containing an enteric polymer. The relation of the alkaline agent to the enteric polymer is 5 to 95% when calculated by the formula:

$$\frac{\text{quantity of alkaline agent in grams in the } ICL \times 100}{(\text{quantity of alkaline agent in grams in the } ICL + \text{quantity of enteric polymer in grams in the } ECL)}.$$

15 Claims, No Drawings

(56) References Cited

U.S. PATENT DOCUMENTS

| | | | |
|---|---|---|---|
| 2013/0266658 A1 | 10/2013 | Weiβ et al. | |
| 2015/0190348 A1 | 7/2015 | Haksar et al. | |
| 2016/0022590 A1 | 1/2016 | Odidi | |
| 2017/0143654 A1* | 5/2017 | Hou | A61K 31/197 |
| 2022/0142930 A1 | 5/2022 | Jain et al. | |
| 2023/0000780 A1 | 1/2023 | Haksar et al. | |
| 2023/0048354 A1 | 2/2023 | Haksar et al. | |

FOREIGN PATENT DOCUMENTS

| | | | |
|---|---|---|---|
| WO | 2008/135090 | 11/2008 | |
| WO | 2011/140446 | 11/2011 | |
| WO | 2014/136494 | 11/2014 | |
| WO | 2015/062640 | 5/2015 | |
| WO | 2016/097170 | 6/2016 | |
| WO | WO-2017012935 A1 * | 1/2017 | A61K 31/18 |
| WO | 2017/182347 | 10/2017 | |
| WO | 2021/115648 | 6/2021 | |
| WO | 2021/115649 | 6/2021 | |

OTHER PUBLICATIONS

International Search Report dated Dec. 18, 2020 in PCT/EP2020/075962, 6 pages.

Liu et al. "A paradigm shift in enteric coating: Achieving rapid release in the proximal small intestine of man", Journal of Controlled Release, vol. 147, 2010, pp. 242-245.

Anonymous, "Stabilized Pharmaceutical Formulation", IP.com, Prior Art Database, Sep. 17, 2002, XP002374253, 3 pages.

Written Opinion dated Dec. 18, 2020 in PCT/EP2020/075962, 9 pages.

U.S. Pat. No. 9,237,760, Jan. 19, 2016, 2010/0247639, Ravishankar et al.

U.S. Appl. No. 12/742,263, filed May 11, 2010, 2010/0255092 Ravishankar et al.

U.S. Pat. No. 10,842,752, Nov. 24, 2020, 2015/0190348, Haksar et al.

U.S. Appl. No. 17/595,145, filed Nov. 10, 2021, 2022/0142930, Jain et al.

Extended European Search Report dated Jul. 8, 2020, in European Application No. 20153758.6, 7 pages.

Extended European Search Report dated Jul. 10, 2020, in European Application No. 20153812.1, 8 pages.

International Search Report dated Dec. 17, 2020, in PCT/EP2020/075960, 6 pages.

International Search Report dated Dec. 17, 2020, in PCT/EP2020/075961, 7 pages.

Written Opinion dated Dec. 17, 2020, in PCT/EP2020/075960, 7 pages.

Written Opinion dated Dec. 17, 2020, in PCT/EP2020/075961, 10 pages.

U.S. Appl. No. 17/757,055, filed Jun. 8, 2022, 2023/0048354, Haksar et al.

U.S. Appl. No. 17/757,060, filed Jun. 8, 2022, 2023/0000780, Haksar et al.

* cited by examiner

DOSAGE FORM FOR USE IN TREATING OR PREVENTING OF A DISEASE

CROSS-REFERENCE TO RELATED APPLICATIONS

This application is the National Stage entry under § 371 of International Application No. PCT/EP2020/075962, filed on Sep. 17, 2020, and which claims the benefit of priority to Indian Application No. 201941051259, filed on Dec. 11, 2019. The content of each of these applications is hereby incorporated by reference in its entirety.

BACKGROUND OF THE INVENTION

Field of the Invention

The invention is in the field of pharmacy and nutraceuticals, especially in the field of dosage forms, comprising a biologically active ingredient, for use in treating or preventing of a disease in the animal or human body.

Background Description of Related Art

U.S. Pat. No. 4,786,505 describes an oral pharmaceutical preparation comprising (a) a core region comprising an effective amount of a material selected from the group of omeprazole plus an alkaline reacting compound, an alkaline omeprazole salt plus an alkaline compound and an alkaline omeprazole salt alone, (b) an inert subcoating which is soluble or rapidly disintegrating in water disposed on said core, said subcoating comprising one or more layers of materials selected from among tablet excipients and polymeric film-forming compounds; and (c) an outer layer disposed on said subcoating comprising an enteric coating. The subcoating layer also serves as a pH-buffering zone. The pH buffering properties of subcoating layer may be further strengthened by introducing substances chosen from a group of compounds usually used in antacid formulations such as, for instance, magnesium oxide, hydroxide or carbonate, aluminium or calcium hydroxide, carbonate or silicate; composite aluminium/magnesium compounds such as, for instance, [$Al_2O_3 \cdot 6MgO \cdot CO_2 \cdot 12H_2O$ or $MgO \cdot AlO_3 \cdot 2SiO_2 \cdot n\text{-}H_2O$], wherein n is not an integer and less than 2. The object of U.S. Pat. No. 4,786,505 is to provide an enteric coated dosage form of omeprazole, which is resistant to dissolution in acid media and which dissolves rapidly in neutral to alkaline media and which has a good stability during long term storage. In examples 1 and 6 of U.S. Pat. No. 4,786,505 the percentage of alkaline substance, (magnesium oxide or aluminium hydroxide/magnesium carbonate) in the subcoating layer, calculated on the weight of alkaline agent and the enteric polymer (hydroxypropyl methylcellulose phthalate) in the enteric coating layer is about 4.1 or 6.6% by weight respectively.

US2005/0214371A1 describes a stable composition of an acid labile drug, comprising a) an inner core with the acid labile drug; b) a first intermediate coating devoid of an alkaline stabilizing agent and the acid labile drug; c) a second intermediate coating comprising an alkaline stabilizing agent; and d) an outer enteric layer, wherein the acid labile drug can degrade at pH 3. The term "acid labile drug" refers to any drug or medicament or active pharmaceutical ingredient (API) that will degrade at a pH of 3. Examples of "acid labile drug" include pharmaceutically active substituted benzimidazole compounds, statins (e.g. pravastatin, fluvastatin and atorvastatin), antibiotics (e.g. penicillin G, ampicillin, streptomycin, clarithromycin and azithromycin), dideoxy cytosine (ddC), digoxin, pancreatin, bupropion and pharmaceutically acceptable salts thereof, such as buprion HCl. The term "pharmaceutically active substituted benzimidazole compound" refers to any pharmaceutically active substituted 2-(2-pyridylmethyl)-sulfinyl-1H-benzimidazole compound (e.g. lansoprazole, omeprazole, hydroxy omeprazole, pantoprazole, rabeprazole, esomeprazole, preprazole, pariprazole, rabeprazole and tenatoprazole) and pharmaceutically active substituted 2-(phenylmethyl)-sulfinyl-1H-benzimidazole compound (e.g. leminoprazole). US2005/0214371A1 does not mention or suggest an unexpected release of the acid labile drugs at low pH values.

US2005/0214371A1 also provides a method of treating a disease selected from gastric or duodenal ulcer, severe erosive esophagitis, Zolinger-Elison syndrome, gastroesophageal reflux and *H. pylori* infection, comprising an effective amount of a stable pharmaceutical composition of the invention to a subject inflicted with the disease, preferably a subject in need of the treatment, wherein the acid labile drug in the stable pharmaceutical composition is selected from lansoprazole, omeprazole, pantoprazole, rabeprazole, hydroxy omeprazole, esomeprazole, pariprazole, preprazole, tenatoprazole, leminoprazole, and acceptable salts thereof.

IPCOM000009757D (IP.com Prior Art Database Technical Disclosure IP.com Number IPCOM000009757D, IP.com electronic publication date Sep. 17, 2002, Authors et al.: Disclosed Anonymously) describes "Stabilized Pharmaceutical Formulation of an Acid labile Benzimidazole Compound and its Preparation". The general disclosure IPCOM000009757D is very similar to that of US2005/0214371A1 with the exception that no "b) a first intermediate coating devoid of an alkaline stabilizing agent and the acid labile drug" is mentioned. IPCOM000009757D is silent about any unexpected early release of the included active pharmaceutical ingredient.

U.S. Pat. No. 7,932,258 B2 describes the use of a partially neutralized (meth)acrylate copolymer as a coating for the production of a medicament pharmaceutical form releasing active substance at reduced pH values.

WO 2008/135090A1 describes dosage forms comprising two individual coatings that may comprise an inner coating comprising a partially neutralized anionic (meth)acrylate copolymer or a water soluble neutral polymer in combination with a C2-C16 carboxylic acid and an outer coating comprising an anionic (meth)acrylate copolymer, which is less neutralized than the material of the inner coating or not neutralized at all. The intended effect is that in vivo the solid dosage form releases its active substance "earlier", namely already at the entry of the intestine. The term "earlier" here means that the solid dosage form according to the invention starts to release the active substance already at lower pH value compared to the normal pH of the intestine, namely when the solid dosage form is transferred from the stomach having low pH to the entry of the intestine (e.g. pH 5.6) which is having a higher pH compared to the stomach, but not as high as it is the case in more distal sections of the intestine. In comparison to a standard EUDRAGIT® L100-55 coating, which shows almost no active ingredient release at pH 5.6, the double coating system releases around 30% of the active ingredient at the same pH in 45 min.

SUMMARY OF THE INVENTION

U.S. Pat. No. 4,786,505, US2005/0214371A1 and IPCOM000009757D provide stable pharmaceutical compositions for acid labile substances such as substituted benzimidazole compounds especially the omeprazole or pantoprazole substance family. To provide pH stability during storage conditions a buffering alkaline substance is included in an intermediate coating layer. An outer enteric coating layer shall protect the substances from contact with the gastric acid. No data are available in U.S. Pat. No. 4,786, 505, US2005/0214371A1 and IPCOM000009757D about the release of biologically active ingredients at pH values being present after the stomach passage. This may be reasoned by the teaching directed to the acid labile character of the chosen substances, for which would it not make too much sense to attempt a release at pH values already between 3 and 5.5.

WO 2008/135090A1 describes dosage forms comprising two individual coatings that may comprise an inner coating comprising a partially neutralized anionic (meth)acrylate copolymer or a water-soluble neutral polymer in combination with a C2-C16 carboxylic acid and an outer coating comprising an anionic (meth)acrylate copolymer, which is less neutralized than the material of the inner coating or not neutralized at all. The intended effect is that in vivo the solid dosage form releases its active substance "earlier", namely already at the entry of the intestine. The effect seems to be limited to pH values not below around pH 5.6.

U.S. Pat. No. 7,932,258 B2 describes the use of a partially neutralized (meth)acrylate copolymer as a coating for the preparing of a medicament pharmaceutical form releasing active substance at reduced pH values. However, in practice the reported effect of the single coating system seems to be alleviated when the compositions are tested first for 2 hours in acidic medium pH 1.2 and then at media with low pH between 3 and 5.5.

SUMMARY OF THE INVENTION

There is a need for dosage forms for use in treating or preventing of a disease in the animal or human body, which treatment or prevention requires the release of 50% or more of the biologically active ingredient in the small intestine within the pH range from 3 to 5.5. The objects of the invention are solved as described below.

Dosage Form

The invention is concerned with a dosage form comprising a biologically active ingredient for use in treating or preventing of a disease in the animal or human body, which treatment or prevention provides the release of 50% or more of the biologically active ingredient in the small intestine within the pH range pH from 3 up to 5.5, wherein the dosage form comprises:

a) a core, comprising the biologically active ingredient, b) an intermediate coating layer (ICL) onto to or above the core, comprising an alkaline agent and c) an enteric coating layer (ECL) onto or above the intermediate coating layer, comprising an enteric polymer, wherein the relation of the alkaline agent to enteric polymer in the dosage form is 5 to 95% when calculated by the formula:

$$\frac{\text{quantity of alkaline agent in grams in the } ICL \times 100}{(\text{quantity of alkaline agent in grams in the } ICL + \text{quantity of enteric polymer in grams in the } ECL)}$$

wherein biologically active ingredients which are proton-pump inhibitors belonging to the class of substituted benzimidazole compounds are excepted.

The dosage form may usually have the form of the core, however additionally coated with the intermediate coating layer and the enteric coating layer as disclosed, e.g. the form of a (coated) pellet (core). Furthermore, several single dosage forms may be contained in multiple as parts of a multi-unit dosage form, e.g. contained in a capsule or in a tablet in which a multiple of inventive dosage form are contained, e.g. in the form of (coated) pellet (cores).

The dosage form may have the form of, for instance, a tablet, a minitablet, a pellet, a pill, a granule, a sachet or a capsule. The dosage form may as well be contained, preferably in multi-units, for instance, in a tablet, in a sachet or in a capsule.

DETAILED DESCRIPTION OF THE INVENTION

Release of the Biologically Active Ingredient

Preferably the release of the biologically active ingredient is 10% or less at pH 1.2 for 120 min and 50% or more (50-100%), preferably 60 to 100%, at a pH from 3 to 5.5, preferably at a pH from 3.2 to 5.0, for 45 min. The pH 1.2 test medium may be 0.1 N HCl according to USP, for instance USP 42, pH 3 to 5.5 media may be buffered media according to USP, for instance USP 42 (2019).

Core

The core of the dosage form comprises a biologically active ingredient.

The core of the dosage form may comprise the biologically active ingredient distributed in a matrix structure or bound in a binder in a coating on an inner core structure or enclosed in a capsule.

The core may be prepared by methods such as granulation, extrusion, spheronization or hot melt extrusion.

The core may be a pellet, a pill a granule, a tablet or a capsule. The core may be an active ingredient-containing tablet, a pellet-containing compressed tablet, a mini-tablet or a capsule, which may be filled with active ingredient-containing pellets or granules, with a drug solution or dispersion, with mini-tablets or powder or combinations thereof.

The core may comprise for instance an uncoated pellet, a neutral carrier pellet, for instance a sugar sphere or nonpareilles, on top of which the biologically active ingredient is bound in a binder, such as lactose, polyvinyl pyrrolidone or a neutral cellulose-derivates such as HPC or HPMC. The binder-coating layer with the biologically active ingredient is considered herein as part of the core.

The binder-coating layer of the core has, in contrast to the intermediate coating layer and the enteric coating layer, essentially no influence on the controlled release of the biologically active ingredient. The core may as well comprise an uncoated pellet consisting of a crystallized biologically active ingredient.

The core may comprise 1 to 100, 2 to 90, 5 to 85, 10 to 70, 15 to 50% by weight of the biologically active ingredient. The core may comprise 0 to 99, 10 to 98, 15 to 95, 30 to 90 or 50 to 85% by weight of pharmaceutical or nutraceutical acceptable excipients. The biologically active ingredient and the pharmaceutical or nutraceutical acceptable excipients may add up to 100%.

The biologically active ingredient may be comprised in the core of the dosage form in an amount from 0.1 to 100% by weight of the core.

Biologically Active Ingredient(s)

The biologically active ingredient(s) may comprise biologically active pharmaceutical ingredients and biologically active nutraceutical ingredients.

Biologically active ingredients which are proton-pump inhibitors belonging to the class of substituted benzimidazole compounds are excepted from the scope of the invention. The term proton-pump inhibitor is well known to a skilled person in the field of pharmacy. The pharmaceutical main action of proton-pump inhibitors is a pronounced and long-lasting reduction of stomach acid production. Thus, the term proton-pump inhibitors belonging to the class of pharmaceutically active means substituted benzimidazole compounds with pharmaceutical proton pump inhibitor activity. Especially the term proton-pump inhibitors belonging to the class of pharmaceutically active substituted benzimidazole compounds refers to pharmaceutically active substituted 2-(2-pyridylmethyl)-sulfinyl-1H-benzimidazole compounds (e.g. lansoprazole, omeprazole, hydroxy omeprazole, pantoprazole, rabeprazole, esomeprazole, preprazole, pariprazole, rabeprazole and tenatoprazole) and pharmaceutically active substituted 2-(phenylmethyl)-sulfinyl-1H-benzimidazole compound (e.g. leminoprazole).

Disease(s)

The disease(s) and the class of biologically active ingredient(s) associated for treating or preventing the disease(s) may be selected from gastrointestinal lavage and a laxatives, inflammatory bowel diseases and corticosteroids, hypercholesterolemia or hypertriglyceridemia and statins, CHF and glycosides, arrhythmia and stereoisomers of quinidine, cancer and plant alkaloids, bacterial infections and antibiotics, HIV and nucleosides, pancreatic insufficiency and lipases, major depressive disorder (MDD) or seasonal affective disorder (SAD) or an aid for smoking cessation and norepinephrine/dopamine-reuptake inhibitors (NDRI), pain and inflammation and NSAIDs, rheumatoid arthritis, osteoarthritis or ankylosing spondylitis and NSAIDs, Parkinson's disease and dopamine precursors, malaria and antimalarials, hypertension and beta-blockers, diabetes and biguanides, edema or chronic renal insufficiency and benzoic-sulfonamide-furans, mild to severe heart failure, left ventricular dysfunction after myocardial infarction with ventricular ejection fraction ≤40% hypertension and beta adrenoceptor blockers, systemic fungal infections and antifungals, hyperlipoproteinemia or hypertriglyceridemia and fibrate antilipemics, heart failure and mineralocorticoid hormones, cancer and Anthracycline antibiotics, hypertension, angina or cluster headache prophylaxis and calcium channel blockers, and atrial fibrillation and beta blockers.

The disease(s) and the biologically active ingredient(s) associated for treating or preventing the disease(s) may be selected from gastrointestinal lavage and bisacodyl, inflammatory bowel diseases and budesonide, hypercholesterolemia or hypertriglyceridemia and fluvastatin, CHF and digoxin, arrhythmia and quinidine, cancer and etoposide, ulcer and gastroesophageal reflux disease (GERD) and omeprazole, lansoprazole, pantoprazole or rabeprazole, bacterial infections and erythromycin, penicillin G, ampicillin, streptomycin, clarithromycin or azithromycin, HIV and dideoxyinosine (ddl or didanosine), dideoxyadenosine (ddA) or dideoxycytosine (ddC), pancreatic insufficiency and lipases, major depressive disorder (MDD) or seasonal affective disorder (SAD) or an aid for smoking cessation and bupropion, pain and inflammation, rheumatoid arthritis, osteoarthritis or ankylosing spondylitis and acetyl salicylic acid (Aspirin®), diclofenac or indomethacin, parkinson's disease and levodopa, malaria and hydroxychloroquine sulphate, hypertension and atenolol, diabetes and metformin hydrochloride, edema or chronic renal insufficiency and benzoic-sulfonamide-furans, mild to severe heart failure, left ventricular dysfunction after myocardial infarction with ventricular ejection fraction ≤40% hypertension and furosemide, systemic fungal infections and ketoconazole, hyperlipoproteinemia or hypertriglyceridemia and fenofibrate, heart failure and aldosteron, cancer and doxorubicin, hypertension, angina or cluster headache prophylaxis and verapamil, and atrial fibrillation and sotalol.

Preferably the disease may be atrial fibrillation and the biologically active ingredient associated for treating or preventing the is sotalol.

Further biologically active ingredients according to the present application may be biotechnology derived products or microbiologically derived products and may be selected from, for instance, enzymes, hormones, liquid or solid natural extracts, oligonucleotides, DNA, RNA, mRNA, siRNA, Protacs (proteolysis targeting chimera), peptide hormones, therapeutic bacteria, prebiotics, probiotics, peptides, proteins, urology drugs, omega-3-fatty acids, anthocyanidines e.g. from bilberries, blueberries or black currants as antioxidants, vitamins and vaccines.

Intermediate Coating Layer

The intermediate coating layer (ICL) is onto to or above the inner core and is comprising an alkaline agent. The intermediate coating layer may comprise 5 to 75, preferably 10 to 50% by weight of the alkaline agent. The intermediate layer may comprise 25 to 95, preferably 90 to 50% by weight of further pharmaceutically or nutraceutically acceptable excipients, such as, for example, a polymeric binder, for instance a neutral water-soluble cellulose such as hydroxypropylmethylcellulose (HPMC) or hydroxypropylcellulose (HPC) or polyvinyl pyrrolidone (PVP), or a plasticizer or a anti tacking agent or combination thereof. The polymeric binder may also be a neutral or an anionic (meth)acrylate copolymer, the latter may optionally be partially or completely neutralized. Preferably the intermediate layer is onto the core with no other coating layers in between. The intermediate coating layer may be present in an amount of 5 to 100, preferably 7.5 to 50% by weight calculated on the weight of the core.

Alkaline Agent

The alkaline agent may be an alkali or an earth alkali metal salt. The alkaline agent may be, for instance, selected from calcium oxide, calcium carbonate, magnesium carbonate, magnesium oxide, sodium carbonate, sodium bicarbonate and sodium hydroxide or any mixtures thereof. Preferred alkaline agents are magnesium oxide or magnesium carbonate. The relation of the alkaline agent in the intermediate coating layer (ICL) to the enteric polymer in the enteric coating layer (ECL) is 5 to 95, preferably 7 to 80% when calculated by the formula:

$$\frac{\text{quantity of alkaline agent in grams in the } ICL \times 100}{\text{(quantity of alkaline agent in grams in the } ICL + \text{quantity of enteric polymer in grams in the } ECL\text{)}}$$

Plasticizers

Plasticizers may be defined in that they achieve through physical interaction with a polymer a reduction in the glass transition temperature and promote film formation, depending on the added amount. Suitable substances usually have a molecular weight of between 100 and 20,000 and comprise one or more hydrophilic groups in the molecule, e.g. hydroxy ester or amino groups.

The intermediate coating layer or the enteric coating layer may comprise a plasticizer, which may be selected from the groups of alkyl citrates, glycerol esters, alkyl phthalates, alkyl sebacates, sucrose esters, sorbitan esters and polyethylene glycols. The intermediate coating layer may comprise a plasticizer, preferably about 2 to 50, preferably 5 to 25% by weight, which may be selected for instance from triethyl citrate (TEC), acetyl triethyl citrate (ATEC), diethyl sebacate and dibutyl sebacate (DBS), glycerol, propylene glycol, polyethylene glycols 200 to 12,000 and castor oil. A preferred plasticizer for the intermediate coating layer may be glycerine or triethyl citrate. A preferred plasticizer for the enteric coating layer may be triethyl citrate.

Enteric Coating Layer

The enteric coating layer is onto to or above the intermediate coating layer is comprising an enteric polymer and optionally pharmaceutically or nutraceutically acceptable excipients. The enteric coating layer may comprise 10 to 100, preferably 20 to 80% by weight of the enteric polymer. The enteric coating layer may comprise 90 to 0, preferably 80 to 20% by weight of pharmaceutically or nutraceutically acceptable excipients, such as, for example, a plasticizer. Preferably the enteric coating layer is onto the intermediate coating layer with no other coating layers in between. The enteric coating layer may be present in an amount of 5 to 50% by weight calculated on the weight of the core and the intermediate layer.

Enteric Polymer

The enteric polymer in the further coating layer onto or above the intermediate coating layer may be selected from anionic (meth)acrylate copolymers, anionic celluloses, anionic polysaccharides and polyvinyl acetate phthalates or any mixtures thereof. The enteric coating layer may be present in an amount of 10 to 50% by weight calculated on the weight of the core and the intermediate layer.

Anionic (Meth)Acrylate Copolymer(s)

The enteric coating layer may comprise a (meth)acrylate copolymer selected from copolymers comprising polymerized units of methacrylic acid and ethyl acrylate, of methacrylic acid and methyl methacrylate, of ethyl acrylate and methyl methacrylate or of methacrylic acid, methyl acrylate and methyl methacrylate, from a mixture of a copolymer comprising polymerized units of methacrylic acid and ethyl acrylate with a copolymer comprising polymerized units of methyl methacrylate and ethyl acrylate and a mixture of a copolymer comprising polymerized units of methacrylic acid, methyl acrylate and methyl methacrylate with a copolymer comprising polymerized units of methyl methacrylate and ethyl acrylate or any mixtures thereof.

The coating layer may comprise a (meth)acrylate copolymer comprising polymerized units of 40 to 60% by weight of methacrylic acid and 60 to 40% by weight of ethyl acrylate (type EUDRAGIT® L 100-55). A suitable second polymer is EUDRAGIT® L 100-55 (Evonik Nutrition & Care GmbH, Darmstadt, Germany), which is a copolymer comprising polymerized units of 50% by weight of methacrylic acid and 50% by weight of ethyl acrylate. EUDRAGIT® L 30 D-55 is a 30% by weight aqueous dispersion of EUDRAGIT® L 100-55. The glass transition temperature $T_{gm}$ of EUDRAGIT® L 100-55 is about 110° C.

The coating layer may comprise a (meth)acrylate copolymer comprising polymerized units of 5 to 15% by weight methacrylic acid, 60 to 70% by weight of methyl acrylate and 20 to 30% by weight methyl methacrylate (type EUDRAGIT® FS). A suitable copolymer is EUDRAGIT® FS which is a copolymer polymerized from 25% by weight of methyl methacrylate, 65% by weight of methyl acrylate and 10% by weight of methacrylic acid. EUDRAGIT® FS 30 D is a dispersion comprising 30% by weight EUDRAGIT® FS. The glass transition temperature $T_{gm}$ of EUDRAGIT® FS is about 45° C.

The coating layer may comprise a (meth)acrylate copolymer comprising polymerized units of 40 to 60% by weight of methacrylic acid and 60 to 40% by weight of methyl methacrylate (type EUDRAGIT® L 100). EUDRAGIT® L 100 is a copolymer polymerized from 50% by weight of methyl methacrylate and 50% by weight of methacrylic acid. The glass transition temperature $T_{gm}$ of EUDRAGIT® L 100 is about or somewhat above 150° C.

The coating layer may comprise a (meth)acrylate copolymer comprising polymerized units of 20 to 40% by weight of methacrylic acid and 60 to 80% by weight of methyl methacrylate (type EUDRAGIT® S 100). EUDRAGIT® S 100 is a copolymer polymerized from 70% by weight methyl methacrylate and 30% by weight methacrylic acid. The glass transition temperature $T_{gm}$ of EUDRAGIT® S 100 is about or somewhat above 160° C.

The coating layer may also comprise an anionic (meth) acrylate copolymer(s) in the form of a core-shell polymer from two (meth)acrylate copolymer(s). The coating layer may comprise a (meth)acrylate copolymer which is a core-shell polymer, comprising 50 to 90, preferably 70 to 80% by weight of a core, comprising polymerized units of 60 to 80, preferably 65 to 75% by weight of ethyl acrylate and 40 to 20, preferably 35 to 25% by weight of methyl methacrylate, and 50 to 10, preferably 30 to 20% by weight of a shell, comprising polymerized units of 40 to 60, preferably 45 to 55% by weight of ethyl acrylate and 60 to 40, preferably 55 to 45% by weight of methacrylic acid.

A suitable core-shell polymer is EUDRAGIT® FL 30 D-55 (Evonik Nutrition & Care GmbH, Darmstadt, Germany), which is a commercially available 30% by weight aqueous dispersion of a copolymer from a two-stage emulsion polymerization process, with a core of about 75% by weight, comprising polymerized units of about 70% by weight of ethyl acrylate and 30% by weight of methyl methacrylate, and a shell of about 25% by weight, comprising polymerized units of 50% by weight ethyl acrylate and 50% by weight methacrylic acid. The glass transition temperature $T_{gm}$ of the polymer of EUDRAGIT® FL 30D-55 is about 8° C.

Anionic Celluloses

Anionic celluloses (chemically modified celluloses) may be selected from carboxymethyl ethyl cellulose and its salts, cellulose acetate phthalate, cellulose acetate succinate, cellulose acetate trimellitate, hydroxypropyl methyl cellulose phthalate and hydroxypropyl methyl cellulose acetate succinate or any mixtures thereof.

Anionic Polysaccharides

Anionic polysaccharides (not based on cellulose) with enteric properties may be selected from polymers such as shellac, chitosan, alginic acid and salts of alginic acid, e.g. sodium, potassium or ammonium alginate.

Pharmaceutically or Nutraceutically Acceptable Excipients

The core, in the intermediate layer or in the enteric coating layer may optionally comprise pharmaceutically or nutraceutically acceptable excipients. Such pharmaceutically or nutraceutically acceptable excipients may be selected from the group of antioxidants, brighteners, binding agents, such as lactose, polyvinyl pyrrolidone or neutral celluloses, flavoring agents, flow aids, glidants, penetrationpromoting agents, pigments, plasticizers, further polymers, pore-forming agents and stabilizers or any combinations thereof.

Items

The invention may be characterized by the following items:

1. Dosage form, comprising a biologically active ingredient for use in treating or preventing of a disease in the animal or human body, which treatment or prevention requires the release of 50% or more of the biologically active ingredient in the small intestine within the pH range from 3 up to 5.5, wherein the dosage form comprises:
   a) a core, comprising the biologically active ingredient,
   b) an intermediate coating layer (ICL) onto or above the core, comprising an alkaline agent and
   c) an enteric coating layer (ECL) onto or above the intermediate coating layer, comprising an enteric polymer,
   wherein the relation of the alkaline agent to the enteric polymer is 5 to 95% when calculated by the formula:

$$\frac{\text{quantity of alkaline agent in grams in the } ICL}{(\text{quantity of alkaline agent in grams in the } ICL + \text{quantity of enteric polymer in grams in the } ECL)} \times 100$$

wherein biologically active ingredients which are proton-pump inhibitors belonging to the class of substituted benzimidazole compounds are excepted.

2. Dosage form according to item 1, wherein the release of the biologically active ingredient is 10% or less at pH 1.2 for 120 min and 50% or more at a pH from 3 to 5.5 for 45 min.

3. Dosage form, according to item 1 or 2, wherein the disease(s) and the class of biologically active ingredients for treating or preventing the disease(s) are selected from gastrointestinal lavage and laxatives, inflammatory bowel diseases and corticosteroids, hypercholesterolemia or hypertriglyceridemia and statins, CHF and glycosides, arrhythmia and stereoisomers of quinidine, cancer and plant alkaloids, bacterial infections and antibiotics, HIV and nucleosides, pancreatic insufficiency and lipases, major depressive disorder (MDD) or seasonal affective disorder (SAD) or an aid for smoking cessation and norepinephrine/dopamine-reuptake inhibitors (NDRI), pain or inflammation and NSAIDs, rheumatoid arthritis, osteoarthritis or ankylosing spondylitis and NSAIDs, Parkinson's disease and dopamine precursors, malaria and antimalarials, hypertension and beta-blockers, diabetes and biguanides, edema or chronic renal insufficiency and benzoic-sulfonamide-furans, mild to severe heart failure, left ventricular dysfunction after myocardial infarction with ventricular ejection fraction ≤40% hypertension and beta adrenoceptor blockers, systemic fungal infections and antifungals, hyperlipoproteinemia or hypertriglyceridemia and fibrate antilipemics, heart failure and mineralocorticoid hormones, cancer and anthracycline antibiotics, hypertension, angina or cluster headache prophylaxis and calcium channel blockers, and atrial fibrillation and beta blockers.

4. Dosage form, according to any of items 1 to 3, wherein the disease(s) and the biologically active ingredient associated for treating or preventing the disease(s) are selected from gastrointestinal lavage and bisacodyl, inflammatory bowel diseases and budesonide, hypercholesterolemia or hypertriglyceridemia and fluvastatin, CHF and digoxin, arrhythmia and quinidine, cancer and etoposide, bacterial infections and erythromycin, penicillin G, ampicillin, streptomycin, clarithromycin or azithromycin, HIV and dideoxyinosine (ddl or didanosine), dideoxyadenosine (ddA) or dideoxycytosine (ddC), pancreatic insufficiency and lipases, major depressive disorder (MDD) or seasonal affective disorder (SAD) or an aid for smoking cessation and bupropion, pain and inflammation, rheumatoid arthritis, osteoarthritis or ankylosing spondylitis and acetyl salicylic acid (Aspirin®), diclofenac or indomethacin, parkinson's disease and levodopa, malaria and hydroxychloroquine sulphate, hypertension and atenolol, diabetes and metformin hydrochloride, edema or chronic renal insufficiency and benzoic-sulfonamide-furans, mild to severe heart failure, left ventricular dysfunction after myocardial infarction with ventricular ejection fraction ≤40% hypertension and furosemide, systemic fungal infections and ketoconazole, hyperlipoproteinemia or hypertriglyceridemia and fenofibrate, heart failure and aldosteron, cancer and doxorubicin, hypertension, angina or cluster headache prophylaxis and verapamil, and atrial fibrillation and sotalol.

5. Dosage form according to any of items 1 to 4, wherein the disease is atrial fibrillation and the biologically active ingredient for treating or preventing the disease is sotalol.

6. Dosage form, according to one or more of items 1 to 5, wherein the core comprises the biologically active ingredient distributed in a matrix structure or bound in a binder in a coating on an inner core.

7. Dosage form, to one or more of items 1 to 6, wherein the alkaline agent is an alkali or an earth alkali metal salt.

8. Dosage form, according to one or more of items 1 to 7, wherein the alkaline agent is selected from calcium oxide, calcium carbonate, magnesium carbonate, magnesium oxide, sodium carbonate, sodium bicarbonate and sodium hydroxide or any combinations thereof.

9. Dosage form, according to one or more of items 1 to 8, wherein the alkaline agent is magnesium carbonate or magnesium oxide.

10. Dosage form, according to one or more of items 1 to 9, wherein the intermediate coating layer further comprises a plasticizer and/or a polymeric binder.

11. Dosage form, according to one or more of items 1 to 10, wherein the enteric polymer in the enteric coating layer is selected from anionic (meth)acrylate copolymers, anionic celluloses, anionic polysaccharides and polyvinyl acetate phthalates or any mixtures thereof.

12. Dosage form, according to one or more of items 1 to 11, wherein the anionic (meth)acrylate copolymers are selected from copolymers comprising polymerized units of methacrylic acid and ethyl acrylate, of methacrylic acid and methyl methacrylate and of methacrylic acid, methyl acrylate and methyl methacrylate or any mixtures thereof.

13. Dosage form, according to one or more of items 1 to 12, wherein the anionic celluloses are selected from carboxymethyl ethyl cellulose and its salts, cellulose acetate phthalate, cellulose acetate succinate, cellulose acetate trimellitate, hydroxypropyl methyl cellulose phthalate and hydroxypropyl methyl cellulose acetate succinate or any mixtures thereof.

14. Dosage form, according to one or more of items 1 to 13, wherein the relation of the alkaline agent to the enteric polymer is 7 to 80%.

15. Dosage form according to one or more of the preceding items, wherein the release of the biologically active ingredient is 10% or less at pH 1.2 for 120 min and 60 to 100% within the pH from 3.2 to 5.0 for 45 min.

16. Dosage form according to one or more of the preceding items, wherein core comprises 0.1 to 100, 1 to 100, 2 to 90, 5 to 85, 10 to 70 or 15 to 50% by weight of the biologically active ingredient.

17. Dosage form according to one or more of the preceding items, wherein the core comprises 0 to 99.9, 0 to 99, 10 to 98, 15 to 95, 30 to 90 or 50 to 85% by weight of pharmaceutical or nutraceutical acceptable excipients.

18. Dosage form according to one or more of the preceding items, wherein the biologically active ingredient is selected from acetyl salicylic acid, benazepril, bisascodyl, budesonide, carvediol, etopside, quinidine, ketoconazole or sotalol, enzymes, hormones, liquid or solid natural extracts, oligonucleotides, DNA, RNA, mRNA, siRNA, Protacs (proteolysis targeting chimera), peptide hormones, therapeutic bacteria, prebiotics, probiotics, peptides, proteins, urology drugs, omega-3-fatty acids and their salts, anthocyanines e.g. from bilberries, blueberries or black currants, vitamins and vaccines.

19. Dosage form according to one or more of the preceding items, wherein the intermediate coating layer (ICL) is present in an amount of 5 to 100% by weight calculated on the weight of the core.

20. Dosage form according to one or more of the preceding items, wherein the intermediate coating layer (ICL) is present in an amount of 7.5 to 50% by weight calculated on the weight of the core.

21. Dosage form according to one or more of the preceding items, wherein the intermediate coating layer (ICL) comprises 5 to 75% by weight of the alkaline agent.

22. Dosage form according to one or more of the preceding items, wherein the intermediate coating layer (ICL) comprises 10 to 50% by weight of the alkaline agent.

23. Dosage form according to one or more of the preceding items, wherein the enteric coating layer (ECL) is present in an amount of 10 to 50% by weight calculated on the weight of the core and the intermediate layer.

24. Dosage form according to one or more of the preceding items, wherein the enteric coating layer (ECL) comprises 10 to 100% by weight of the enteric polymer.

25. Dosage form according to one or more of the preceding items, wherein the enteric coating layer (ECL) comprises 20 to 80% by weight of the enteric polymer.

26. Dosage form according to one or more of the preceding items, wherein the enteric polymer comprises a (meth) acrylate copolymer comprising polymerized units of 40 to 60% by weight of methacrylic acid and 60 to 40% by weight of ethyl acrylate.

EXAMPLES

A. Core Preparation:
1. Benazepril (Core) tablets:
1.1 Composition for Benazepril Tablets:

TABLE 3

Composition of Benazepril tablets:

| | Experiment ID | |
|---|---|---|
| | I1 & I2 | I1 |
| | Composition | Composition |
| Ingredients | (% w/w) | (mg/tablet) |
| Intra-granular materials | | |
| Benazepril Hydrochloride | 20 | 40.00 |
| Microcrystalline Cellulose PH101 | 30 | 60.00 |
| Lactose monohydrate | 10 | 20.00 |
| HPMC 6 cps | 2.4 | 4.80 |
| Water | q.s* | q.s* |
| Extra-granular materials | | |
| Microcrystalline Cellulose PH102 | 29.9 | 59.80 |
| Aerosil® 200 Pharma | 1.1 | 2.20 |
| Croscarmellose sodium | 5.5 | 11.00 |
| Magnesium stearate | 1.1 | 2.20 |
| Total | 100 | 200.00 |
| Solid content of binder solution | 5.5% w/w | 5.5% w/w |
| Water uptake | 33% w/w | 33% w/w |

*q.s. to achieve granulation end point
* Note:
Composition of Experiment I1 is also expressed in mg for demonstrating Percentage alkali on alkali and enteric polymer calculation. Quantities of ingredients in subsequent experiments can be calculated likewise.
Abbreviations:
HPMC: Hydroxy propyl methyl cellulose 1.2 Process for Benazepril tablets:
I. Weigh all the ingredients as specified in the formula.
II. Benazepril hydrochloride and lactose monohydrate were mixed uniformly and sifted through #40 mesh.
III. Microcrystalline cellulose PH101 and half quantity of HPMC 6 cps was sifted through #40 mesh and added to the step II.
IV. The powder blend of step III was added in to rapid mixture granulator and mixed for 5 min at slow speed.
V. In a separate beaker, remaining half quantity of HPMC 6 cps was added slowly in purified water under continuous stirring to get a clear binder solution.
VI. Step V binder solution was then used to granulate dry mix of step IV.
VII. After granulation, sift the wet material through 10 # (2.0 mm) sieve.
VIII. Granules were dried in tray dryer at 50° C. until LOD was achieved below 5% w/w.
IX. Dried granules were passed through 30 # (595 μm) sieve.
X. Weighed all extra-granular materials accurately.
XI. MCC PH 102, Croscarmellose sodium & Aerosil 200 were mixed in polybag and sifted through #40 mesh.
XII. Benazepril granules of step IX & sifted material of step XI were mixed in a double cone blender for 15 min at 15 RPM.
XIII. Sifted magnesium stearate (60 #) was added to step XII for lubrication of the blend for 3 min at 15 RPM in double cone blender.
XIV. Lubricated blend was used for tablet compression.

TABLE 4

General Process Parameters of for Benazepril Tablet preparation:

| General Process Parameters | | Experiment I1 & I2 |
|---|---|---|
| *Granulation* | | |
| Equipment | | Rapid mixer granulator |
| *Process data* | | |
| Dry mixing | Time | 10 minutes |
| | Impeller Speed | Slow |
| | Chopper Speed | . . . |
| Binder addition | Time | 3 minutes |
| | Impeller Speed | Slow |
| | Chopper Speed | . . . |
| Wet mixing | Time | 45 Seconds |
| | Impeller Speed | Slow |
| | Chopper Speed | Slow |
| *Compression* | | |
| Equipment | | Parle Elisabeth Tablet compression machine (ElizaPress-200) |
| *Equipment setup* | | |
| Shape of punch | | Circular, standard concave |
| Size of punch | | 8.0 mm |
| Upper punch | | Plain |
| Lower punch | | Plain |
| *Process data* | | |
| Weight of tablet | mg | 200.0 |
| Hardness | N | 70-90 |
| Thickness | Mm | 3.90-4.10 |
| Friability | % | 0. |
| Disintegration time | Minute | 4-6 |

2. Sotalol (Core) Tablets:

2.1 Composition of Sotalol Tablets:

TABLE 5

Composition of Sotalol tablets:

| Experiment ID | I3 |
|---|---|
| Ingredients | Composition (% w/w) |
| *Intra-granular materials* | |
| Sotalol Hydrochloride | 40 |
| Microcrystalline cellulose PH101 | 30 |
| Ac-Di-Sol ® (Croscarmellose sodium) | 2.5 |
| HPMC 3 cps | 1.5 |
| Water (q.s. to % w/w solids) | q.s* |
| *Extra-granular materials* | |
| Microcrystalline cellulose PH102 | 22.0 |
| Aerosil ® 200 Pharma | 1.0 |
| Croscarmellose sodium | 2.5 |
| Magnesium stearate | 0.5 |
| Total | 100 |
| Solid content of binder solution | 6.5% w/w |
| Water uptake | 30% w/w |

*q.s. to achieve granulation end point 2.2 Process for Sotalol tablets:

I. Weigh all the ingredients as specified in the formula.

II. Sotalol hydrochloride, microcrystalline cellulose and Ac-Di-Sol© were mixed uniformly and sifted through #30 mesh.

III. The powder blend of step II was added in to rapid mixture granulator and mixed for 3 min at slow speed.

IV. In a separate beaker, HPMC 3 cps was added slowly in purified water under continuous stirring to get a clear solution.

V. Step IV solution was then used to granulate dry mix of step III

VI. Granules were dried in tray dryer at 60° C. for 2 hr then passed through 30 # sieve and then further dried for 4 hr at 60° C. till LOD was achieved below 5% w/w.

VII. Dried granules were passed through 30 # (595 μm) sieve.

VIII. Weighed all extra-granular materials accurately.

IX. Microcrystalline cellulose PH101, Ac-Di-Sol® and Aerosil 200 were mixed in polybag and then sifted through #30 mesh.

X. Sotalol granules of step VII & sifted material of step IX were mixed in a double cone blender for 15 min at 15 RPM.

XI. Magnesium stearate (60 # passed) was added to blend of step X and lubricated for 5 min at 15 RPM in double cone blender.

XII. Lubricated blend was used for tablet compression.

TABLE 6

General Process Parameters for Sotalol Tablet preparation

| General Process Parameters | | Experiment I3 |
|---|---|---|
| *Granulation* | | |
| Equipment | | Rapid mixer granulator |
| *Process data* | | |
| Dry mixing | Time | 15 minutes |
| | Impeller Speed | Slow |
| | Chopper Speed | . . . |
| Binder addition | Time | 5 minutes |
| | Impeller Speed | Slow |
| | Chopper Speed | . . . |
| Wet mixing | Time | 1 minute |
| | Impeller Speed | Slow |
| | Chopper Speed | Slow |
| *Compression* | | |
| Equipment | | Parle Elisabeth Tablet compression machine (ElizaPress-200) |
| *Equipment setup* | | |
| Shape of punch | | Circular, standard concave |
| Size of punch | | 8.0 mm |
| Upper punch | | Plain |
| Lower punch | | Plain |
| *Process data* | | |
| Weight of tablet | mg | 200.0 |
| Hardness | N | 60-90 |
| Thickness | Mm | 4.10-4.30 |
| Friability | % | 0.0-0.1 |
| Disintegration time | Minute | 2-4 |

B. Coating:

1. Coating composition for inventive experiments:

TABLE 9

Coating composition for Intermediate and enteric coating of inventive Experiment:

|  | Composition (% w/w) | | | Composition (gram)* |
| --- | --- | --- | --- | --- |
| Experiment No. | I1 | I2 | I3 | I1 |
| Core | BT | BT | ST | 600.00 |
| Intermediate coating step | | | | |
| HPMC (3 cps) | 40.0 | 40.0 | 40.0 | 15.66 |
| Glycerin | 20.0 | 20.0 | 20.0 | 7.83 |
| Magnesium oxide | 40.0 | ... | 40.0 | 15.66 |
| Magnesium Carbonate | ... | 40.0 | ... | ... |
| Water (q.s to % w/w solid) | q.s. to 10% | q.s. to 10% | q.s. to 10% | 352.35 |
| Total | 100 | 100 | 100 | 639.15 |
| Polymer build up w.r.t. core pellets/tablets | 3 mg/cm² | 3 mg/cm² | 15 mg/cm² | 3 mg/cm² |
| Enteric coating step | | | | |
| EUDRAGIT L30D-55 | 62.5 | 62.5 | 62.5 | 26.55 |
| TEC | 6.25 | 6.25 | 6.25 | 2.65 |
| Talc | 31.25 | 31.25 | 31.25 | 13.27 |
| Water (q.s to % w/w solid) | q.s. to 20% | q.s. to 20% | q.s. to 20% | q.s. to 20% |
| Total | 100 | 100 | 100 | 681.62 |
| Polymer build up w.r.t. intermediate coated pellets/tablets | 5 mg/cm² | 5 mg/cm² | 4 mg/cm² | 5 mg/cm² |

* Note:
Composition of Experiment I1 is also expressed in grams for demonstrating Percentage alkali on alkali and enteric polymer calculation. Quantities of ingredients in subsequent experiments can be calculated likewise.
Abbreviations:
PP: Pantoprazole pellets;
BT: Benazepril Tablets;
ST: Sotalol Tablets;
PT: Pantoprazole Tablets;
HPMC: Hydroxy propyl methyl cellulose;
TEC: Triethyl Citrate;
w.r.t.: with respect to 2. Coating process for inventive experiments:

2.1 Intermediate coating:

2.1.1 Intermediate coating of experiment I1 & I3:

I. All ingredients were weighed in required quantity.

II. HPMC [3 cps] was dissolved in water containing glycerin using overhead stirrer, until a clear solution is obtained.

III. Magnesium oxide was added to above solution slowly while stirring and resulted suspension was then allowed to mix for 30 min.

IV. Suspension was passed through 100 # sieve and used for intermediate coating.

2.1.2 Intermediate coating of experiment I2:

I. All ingredients were weighed in required quantity.

II. HPMC [3 cps] was dissolved in water containing glycerin using overhead stirrer, until a clear solution is obtained.

III. Magnesium Carbonate was added to above solution slowly while stirring and resulted suspension then was allowed to mix for 30 min.

IV. Suspension was passed through 40 # sieve and used for intermediate coating.

TABLE 10

General Process Parameters for intermediate coating of inventive Experiment I1 to I3:

| General Process Parameters for intermediate coating | | Experiment I1-I3 |
| --- | --- | --- |
| Equipment used | | Neocota |
| Equipment setup | | |
| Silicone tube inner diameter | mm | 3.0 |
| Pan size | inch | 14 |
| Number of baffles | No.s | 6 |
| Process data | | |
| Pan RPM | RPM | 2-8 |
| Inlet temperature | ° C. | 70-73 |
| Product temperature | ° C. | 40-42 |
| Atomization pressure | bar | 1.5 |
| Spray rate | g/min | 3-5 |

2.2 Enteric coating:

2.2.1 Enteric coating of Experiment I1-I3:

I. All the ingredients were weighed in required quantity.

II. TEC and Talc were homogenized in water for 15 min then added slowly to the EUDRAGIT® L 30 D-55 dispersion while stirring, resulted suspension was mixed for 30 min using overhead stirrer.

III. Suspension was passed through 40 # sieve and used for enteric coating.

TABLE 11

General Process Parameters for enteric coating of inventive Experiment I1 to 13:

| General Process Parameters for enteric coating | | Experiment I1-I3 |
| --- | --- | --- |
| Equipment used | | Neocota |
| Equipment setup | | |
| Silicone tube inner diameter | mm | 3.0 |
| Pan size | inch | 14 |
| Number of baffles | No.s | 6 |
| Process data | | |
| Pan RPM | RPM | 8-9 |
| Inlet temperature | ° C. | 45-50 |
| Product temperature | ° C. | 28-32 |
| Atomization pressure | bar | 1.2 |
| Spray rate | g/min | 3-4 |

C. Analysis of enteric coated pellets/tablets:
ANALYTICAL METHODOLOGY
1. Benazepril Tablets
  A) Dissolution Conditions
  1) Dissolution Parameters
  Apparatus: USP Type II
  Dissolution Medium: Acid stage medium for 2 hrs followed by buffer stage medium (1 hr)
  Volume of Medium: 750 mL for acid stage, 1000 mL for buffer stage
  Speed: 50 rpm
  Temperature: 37° C.±0.5° C.
  Withdrawal Volume: 10 ml 2) Dissolution mediums
I. Acid stage medium—0.1 N HCl; Buffer stage medium—pH 5.5 buffer
II. Acid stage medium—0.1 N HCl; Buffer stage medium—pH 4.5 buffer
III. Acid stage medium—0.1 N HCl; Buffer stage medium—pH 3.0 buffer 3) Composition of dissolution mediums
1) Buffer pH 5.5—
1 g of Potassium dihydrogen phosphate, 2 g of Di-potassium hydrogen phosphate and 8.5 g of Sodium chloride was weighed and transferred to 1 liter beaker. To this, 500 mL water was added, salts were dissolved and volume was made up to 1000 mL with water. The pH was adjusted to 5.5 (±0.05) using ortho-phosphoric acid 2) Buffer pH 4.5—
1 g of Potassium dihydrogen phosphate, 2 g of Di-potassium hydrogen phosphate and 8.5 g of Sodium chloride was weighed and transferred to 1 liter beaker. To this, 500 mL water was added, salts were dissolved and volume was made up to 1000 mL with water. The pH was adjusted to 4.5 (±0.05) using ortho-phosphoric acid 3) Buffer pH 3.0—
1 g of Potassium dihydrogen phosphate, 2 g of Di-potassium hydrogen phosphate and 8.5 g of Sodium chloride was weighed and transferred to 1 liter beaker. To this, 500 mL water was added, salts were dissolved and volume was made up to 1000 mL with water. The pH was adjusted to 3.0 (±0.05) using ortho-phosphoric acid 4) Dissolution Procedure:
Acid Stage: Benazepril hydrochloride tablets were transferred in different dissolution jars and then the dissolution test was performed as per parameters given in the method above (Acid Stage). After 2 hours 10 mL of aliquot was removed and analysed as acid stage sample solution.
Buffer Stage: The tablets after acid stage were transferred to buffer stage medium. The dissolution test was continued as per parameters given in the method above (Buffer Stage). The aliquots of each interval ware filtered through 0.45 μm nylon membrane syringe filter discarding first few mL of the filtrate and analysed as buffer stage sample solution.

B) Chromatographic Conditions
Column: Agilent Zorbax Eclipse XDB C18 column, 150×4.6 mm, 5 μm or equivalent
Mobile Phase: Buffer: MeOH (36:64)
Wavelength: 240 nm
Column Temp: 25° C.
Injection Volume: 20 μL
Flow rate: 1 mL/minute
Preparation of Buffer for Mobile Phase:
Accurately weighed 2.25 g of Tetra butyl ammonium bromide transferred in 500 mL water and dissolved. 0.55 mL of Glacial acetic acid added to it and volume was made up to 1000 mL with water. The buffer was filtered through 0.45 μm nylon membrane filter.

2. Sotalol Tablets
A) Dissolution Conditions
1) Dissolution Parameters
Apparatus: USP Type II
Dissolution Medium: Acid stage medium for 2 hrs followed by buffer stage medium (1 hr)
Volume of Medium: 750 mL for acid stage, 1000 mL for buffer stage
Speed: 50 rpm
Temperature: 37° C.±0.5° C.
Withdrawal Volume: 10 ml 2) Dissolution mediums
IV. Acid stage medium—0.1 N HCl; Buffer stage medium—pH 5.5 buffer
V. Acid stage medium—0.1 N HCl; Buffer stage medium—pH 4.5 buffer
VI. Acid stage medium—0.1 N HCl; Buffer stage medium—pH 3.0 buffer 3) Composition of dissolution mediums
1) Buffer pH 5.5—
1 g of Potassium dihydrogen phosphate, 2 g of Di-potassium hydrogen phosphate and 8.5 g of Sodium chloride was weighed and transferred to 1 liter beaker. To this, 500 mL water was added, salts were dissolved and volume was made up to 1000 mL with water. The pH was adjusted to 5.5 (±0.05) using ortho-phosphoric acid 2) Buffer pH 4.5—
1 g of Potassium dihydrogen phosphate, 2 g of Di-potassium hydrogen phosphate and 8.5 g of Sodium chloride was weighed and transferred to 1 liter beaker. To this, 500 mL water was added, salts were dissolved and volume was made up to 1000 mL with water. The pH was adjusted to 4.5 (±0.05) using ortho-phosphoric acid 3) Buffer pH 3.0—
1 g of Potassium dihydrogen phosphate, 2 g of Di-potassium hydrogen phosphate and 8.5 g of Sodium chloride was weighed and transferred to 1 liter beaker. To this, 500 mL water was added, salts were dissolved and volume was made up to 1000 mL with water. The pH was adjusted to 3.0 (±0.05) using ortho-phosphoric acid 4) Dissolution Procedure:
Acid Stage: Sotalol tablets were transferred in different dissolution jars and then the dissolution test was performed as per parameters given in the method above (Acid Stage). After 2 hours 10 mL of aliquot was removed and analyzed as acid stage sample solution. Buffer Stage: The tablets after acid stage were transferred to buffer stage medium. The dissolution test was continued as per parameters given in the method above (Buffer Stage). The aliquots of each interval ware filtered through 0.45 μm nylon membrane syringe filter discarding first few mL of the filtrate and analyzed as buffer stage sample solution.

B) Chromatographic Conditions
Column: Agilent Zorbax Eclipse XDB C 18 column, 150×4.6 mm, 5 μm or equivalent
Mobile Phase: Buffer: ACN (90:10)
Wavelength: 238 nm
Column Temp: 25° C.
Injection Volume: 20 μL
Flow rate: 1.5 mL/minute
Preparation of Buffer for Mobile Phase:
Accurately weighed 6.8 g of potassium dihydrogen ortho-phosphate was dissolved in 1000 mL water. The buffer was filtered through 0.45 μm nylon membrane filter.

D. Summarization:

TABLE 12

Performance of inventive experiments:

| Experiment No. | I1 | I2 | I3 |
|---|---|---|---|
| Objective | Experiment with different alkalis in intermediate layer on acid stable drug & tablet dosage form | | Experiment with very high concentration of alkali in intermediate layer |
| Core | BT | BT | BT |
| Inner layer (Intermediate coat) | 3 mg/cm$^2$ coating of HPMC 3 cps + Glycerol (50%) + MgO(100%) | 3 mg/cm$^2$ coating of HPMC 3cps + Glycerol (50%) + MgCO3 (100%) | 15 mg/cm$^2$ coating of HPMC 3cps + Glycerol (50%) + MgO (100 %) |
| Outer layer (Enteric coat) | 5 mg/cm$^2$ coating of EUDRAGIT L30D-55 + TEC (10%) +Talc (50%) | 5 mg/cm$^2$ coating of EUDRAGIT L30D-55 + TEC (10%) +Talc (50%) | 4 mg/cm$^2$ coating of EUDRAGIT L30D-55 + TEC (10%) + Talc (50%) |
| Dissolution testing in acid media | | | |
| Enteric protection # | Pass | Pass | Pass |
| Dissolution testing in buffer media of respective pH | | | |
| pH 5.5* | 92.5 | 92.2 | 98.7 |
| pH 4.5* | .. | 86.4 | 89.2 |
| pH 4.0* | 90.2 | .. | .. |
| pH 3.0* | 97.6 | .. | 99.3 |
| % alkali in alkali + enteric polymer** | +37% w/w*** | 37% w/w | 77% w/w |
| Inference | Enteric resistance followed by release in pH 3.0, 4.0 & 5.5 demonstrated with acid stable drug for tablet dosage form | Enteric resistance followed by release in pH 4.5 & 5.5 demonstrated with MgCO3 as alkali in intermediate layer | Higher concentration of alkali can be used without affecting performance |

Enteric protection after 2 hrs exposure to 0.1 N HCl;
*Drug release after 45 mins;
**% alkali in alkali + enteric polymer =
***Percent alkali in alkali + enteric polymer for experiment I1 = $^{15.66+33+0100}/_{+815.66+30+026.55+9}$= 37.1% w/w Abbreviation:
BT: Benazepril Tablets;
ST: Sotalol Tablets;
MgO: Magnesium Oxide;
MgCO3: Magnesium Carbonate;
TEC: Triethyl Citrate;
cps: Centipoise;
Qty.: Quantity;
gm: Grams E. Core preparation:
1. Sotalol Tablets:
   Composition and process for Sotalol Tablets for experiment C1 & C2: Refer Core Preparation of Experiment I3
2. Pantoprazole Pellets:
   2.1 Composition of Pantoprazole Pellets (Drug Layering Method):

TABLE 13

Composition of Pantoprazole Pellets:

| Experiment ID | C3 |
|---|---|
| Ingredients | Composition (% w/w) |
| NPS 20/25# (707 - 841 μm) | 73.42 |
| Pantoprazole Sodium Sesquihydrate eq. to Pantoprazole 20% | 22.58 |
| HPMC 6cps | 4.00 |
| Water (q.s. for % w/w solids) | q.s. for 20.0% |
| Total | 100 |

2.2 Process for Pantoprazole Pellets:
I. All the ingredients were weighed in required quantity.
II. HPMC [6 cps] was dissolved in water using overhead stirrer, until a clear solution is obtained.

III. Pantoprazole Sodium Sesquihydrate was sifted through 40 # (400 μm) sieve and added to solution of step II during continuous stirring. Continued stirring till clear solution is obtained.

IV. Drug solution of step III was sifted through 40 # sieve and used for drug layering on NPS 20/25 #.

TABLE 14

General Process Parameters for Pantoprazole Pellets drug Layering:

| General Process Parameters in GPCG 1.1, bottom spray for drug layering | | Experiment C3 |
|---|---|---|
| Equipment setup | | |
| Silicone tube inner diameter | mm | 3.0 |
| Air distribution plate | — | C |
| Column height | mm | 20 |
| Nozzle bore | mm | 0.8 |
| Process parameter setup | | |
| Filter shaking mode | — | Asynchronous |
| Filter shaking | sec | 5 |
| Filter shaking pause | sec | 50 |
| Air flow mode | — | Auto |
| Process data | | |
| Air flow | CFM | 30-90 |
| Atomization pressure | bar | 1.0-1.4 |
| Inlet temperature | ° C. | 45-50 |
| Product temperature | ° C. | 32-38 |
| Spray rate | g/min | 3-8 |

3. Benazepril pellets:

3.1 Composition of Benazepril (Core) pellets:

TABLE 15

Composition of Benazepril pellets for experiment C4 & C5:

| Formula for → | BENAZEPRIL PELLETS | BENAZEPRIL PELLETS |
|---|---|---|
| Experiment ID | C4 | C5 |
| Ingredients | Composition (% w/w) | Composition (% w/w) |
| NPS 18/20# (850-1000 μm) | 64.05 | .. |
| NPS 20/25# (707-841 μm) | .. | 64.78 |
| Benazepril | 20.52 | 20.11 |
| HPMC [3 cps] | 10.33 | 10.12 |
| Lactose | 2.55 | 2.50 |
| Aerosil 200 | 2.55 | 2.50 |
| Water (q.s. to % w/w solids) | q.s. to 20% | q.s. to 25% |
| Total | 100 | 100 |

Abbreviations:
NPS: Non-pareil seeds,
HPMC: Hydroxy propyl methyl cellulose,
cps: centipoise cps: centipoise 3.2 Process for Benazepril pellets preparation for experiment C4 &C5:

I. All ingredients were weighed accurately.

II. Benazepril hydrochloride and lactose monohydrate were dissolved in sufficient quantity of purified water under continuous string.

III. In a separator beaker, HPMC 3 cps was dissolved in purified water under stirring.

IV. Aerosil® 200 was homogenized in purified water for 15 minutes.

V. Step II solution was added to step Ill under stirring.

VI. Step IV dispersion was then added to step V under stirring.

VII. Step VI suspension was then filtered through #60 mesh and used it for drug layering on NPS.

TABLE 16

General Process Parameters for Benazepril pellets (core) preparation of comparative experiments C4 & C5:

| General Process Parameters in GPCG 1.1, bottom spray | | C4 | C5 |
|---|---|---|---|
| Equipment setup | | | |
| Silicone tube inner diameter | mm | 3.0 | 3.0 |
| Air distribution plat | — | B | B |
| Column height | mm | 20 | 20 |
| Nozzle bore | mm | 0.8 | 0.8 |
| Process parameter setup | | | |
| Filter shaking mode | — | Asynchronous | Asynchronous |
| Filter shaking | sec | 5 | 5 |
| Filter shaking pause | sec | 100 | 100 |
| Air flow mode | — | Auto | Auto |
| Process data | | | |
| Air flow | CFM | 50-75 | 60-80 |
| Atomization pressure | bar | 1.0-1.1 | 1.2 |
| Inlet temperature | ° C. | 25-35 | 50-60 |
| Product temperature | ° C. | 20-25 | 40-44 |
| Spray rate | g/min | 2-8 | 3-13 |

F. Coating:

1. Coating composition for seal, intermediate and enteric coating of comparative Experiments:

TABLE 17

Coating composition for seal coating, intermediate coating and enteric coating for experiment C1 to C5:

| | Composition (% w/w) | | | | |
|---|---|---|---|---|---|
| Experiment No. | C1 | C2 | C3 | C4 | C5 |
| Core | ST | ST | PP | BP | BP |

| | | | Seal coating | | |
|---|---|---|---|---|---|
| HPMC (6 cps) | NA | NA | 40.61 | NA | NA |
| Talc | | | 59.39 | | |
| Water (q.s to % w/w solid) | | | q.s.to 15% | | |
| Total | | | 100 | | |
| Polymer build up | | | 1.7% w/w w.r.t. core pellets | | |
| | | | Intermediate coating | | |
| HPMC 3cps | | | | | 74.07 |
| EUDRAGIT® L30D-55 | | 56.50 | | | |
| Pharmacoat 606 | | | 40.0 | | |
| Triethyl citrate | | 2.82 | | | |
| Glycerin | | | | | 18.52 |
| Tween 80 | | 1.13 | | | |
| Talc | | 28.25 | | | |
| Citric acid | | 11.30 | | | |
| Sodium Hydroxide | NA | q.s* | | NA | |
| Magnesium Oxide | | | | | 7.41 |
| Magnesium Carbonate | | | 60.0 | | |
| Water (q.s to % w/w solid) | | q.s.to 10% | q.s.to 10% | | q.s.to 10% |
| Total | | 100 | 100 | | 100 |
| Polymer build up | | 5 mg/cm² w.r.t. core pellets | 3.16% w/w w.r.t. seal coated pellets | | 10% w/w w.r.t. core pellets |
| | | | Enteric coating | | |
| EUDRAGIT L30D-55 | 62.5 | 62.5 | 64.0 | 62.5 | 62.5 |
| TEC | 6.25 | 6.25 | 6.08 | 6.25 | 6.25 |
| Talc | 31.25 | 31.25 | 26.88 | 31.25 | 31.25 |
| Titanium Dioxide | | | 3.04 | | |
| Sodium Hydroxide | | | | q.s. #@ | |
| Water (q.s to % w/w solid) | q.s.to 20% | q.s.to 10% | q.s.to 20% | q.s.to 20% | q.s.to 20% |
| Total | 100 | 100 | 100 | 100 | 100 |
| Polymer build up | 5 mg/cm² w.r.t. core tablets | 5 mg/cm² w.r.t. intermediate coated pellets | 20% w/w w.r.t. intermediate coated pellets | 15% w/w w.r.t. core pellets | 20% w/w w.r.t. intermediate coated pellets |

\# for 30% Neutralization;
@ Used in the form of 1N NaOH solution
Abbreviations:
ST: Sotalol Tablets;
PP: Pantoprazole Pellets;
BP: Benazepril Pellets;
NA: Not applicable;
w.r.t.: with respect to 2. Process of seal, intermediate and enteric coating:

2.1 Seal coating:

2.1.1 Process of seal coating of Experiment C3:

I. All the ingredients were weighed in required quantity.

II. HPMC [6 cps] was dissolved in water using overhead stirrer, till a clear solution is obtained.

III. Talc was added to step II solution slowly while stirring and resulted suspension was allowed to mix for 30 min.

IV. Suspension was passed through 40 # sieve and used for seal coating.

TABLE 18

General Process Parameters for seal coating of comparative experiment C3:

| General Process Parameters in GPCG 1.1, bottom spray for seal coating | | Experiment C3 |
|---|---|---|
| Equipment setup | | |
| Silicone tube inner diameter | mm | 3.0 |
| Air distribution plate | — | C |
| Column height | mm | 15 |
| Nozzle bore | mm | 0.8 |

TABLE 18-continued

General Process Parameters for seal coating of comparative experiment C3:

| General Process Parameters in GPCG 1.1, bottom spray for seal coating | | Experiment C3 |
|---|---|---|
| Process parameter setup | | |
| Filter shaking mode | — | Asynchronous |
| Filter shaking | sec | 5 |
| Filter shaking pause | sec | 250 |
| Air flow mode | — | Auto |
| Process data | | |
| Air flow | CFM | 50-70 |
| Atomization pressure | bar | 1.0-1.4 |
| Inlet temperature | ° C. | 45-50 |
| Product temperature | ° C. | 33-37 |
| Spray rate | g/min | 3-8 |

2.2 Intermediate coating:

2.2.1 Process of intermediate coating of Experiment C2:

I. Weighed all ingredients accurately.

II. Weighed quantity of talc was dispersed in purified water under homogenizer for 30 min.

III. Separately prepared citric acid solution was added in step II.

IV. 1 N NaOH solution required for neutralization of EUDRAGIT® L30D-55 was prepared.

V. In a separate glass beaker, TEC and Tween 80 were added in warmed purified water till to forms a clear solution.

VI. The step V solution was then added to the step II dispersion under overhead stirrer for 10 to 15 min.

VII. The required quantity EUDRAGIT© L30D-55 was added to step II dispersion and mixed.

VIII. The step VII dispersion was neutralized with step IV solution under continuous stirring to form a clear dispersion with required pH.

IX. Suspension was passed through 40 # sieve and used for intermediate coating.

TABLE 19

General Process Parameters for intermediate coating of comparative experiment C2:

| General Process Parameters for intermediate coating | | Experiment C2 |
|---|---|---|
| Equipment used | | Neocota |
| Equipment setup | | |
| Silicone tube inner diameter | mm | 3.0 |
| Pan size | inch | 14 |
| Number of baffles | No.s | 6 |
| Process data | | |
| Pan RPM | RPM | 2-10 |
| Inlet temperature | ° C. | 55-65 |
| Product temperature | ° C. | 30 |
| Atomization pressure | bar | 1.5 |
| Spray rate | g/min | 1-6 |

2.2.2 Process of intermediate coating of Experiment C3:

I. All the ingredients were weighed in required quantity.

II. Pharmacoat 606 was dissolved in purified water using overhead stirrer.

III. Magnesium Carbonate was added to above solution slowly while stirring and resulted suspension was then allowed to mix for 30 min.

IV. Suspension was passed through 40 # sieve and used for intermediate coating.

TABLE 20

General Process Parameters for intermediate coating of comparative experiment C3:

| General Process Parameters in GPCG 1.1, bottom spray for intermediate coating | | Experiment C3 |
|---|---|---|
| Equipment setup | | |
| Silicone tube inner diameter | mm | 3.0 |
| Air distribution plate | — | C |
| Column height | mm | 20 |
| Nozzle bore | mm | 0.8 |
| Process parameter setup | | |
| Filter shaking mode | — | Asynchronous |
| Filter shaking | sec | 5 |
| Filter shaking pause | sec | 250 |
| Air flow mode | — | Auto |
| Process data | | |
| Air flow | CFM | 50-70 |
| Atomization pressure | bar | 1.0-1.4 |
| Inlet temperature | ° C. | 41-45 |
| Product temperature | ° C. | 33-37 |
| Spray rate | g/min | 3-8 |

2.2.3 Process for experiment C5 intermediate coating:

I. All the ingredients were weighed in required quantity.

II. Glycerin was dissolved in purified water.

III. HPMC (3 cps) was dissolved step II using overhead stirrer, till a clear solution is obtained.

IV. Magnesium oxide was added to above solution slowly while stirring and resulted suspension was allowed to mix for 30 min.

V. Suspension was passed through 40 # sieve and used for intermediate coating on drug layered pellets.

2.3 Enteric coating:

2.3.1 Process of enteric coating of Experiment C1 & C2:

I. Weigh all ingredients as specified in the formula.

II. Weighed quantity of talc was dispersed in purified water under homogenizer for 30 min.

III. In a separate glass beaker, TEC was added in warmed purified water till to forms a clear solution.

IV. The step III solution was added to the step II dispersion under overhead stirrer for 15 min.

V. Weighed quantity EUDRAGIT® L30D-55 dispersion was added in to step IV dispersion and mixed.

V. The prepared dispersion was passed through 40 # sieve and used for enteric coating.

2.3.2 Process of enteric coating of Experiment C3:

I. All the ingredients were weighed in required quantity.

II. TEC and Talc were homogenized in water for 15 min then added slowly to the EUDRAGIT® L 30 D-55 dispersion while stirring, resulted suspension was mixed for 30 min using overhead stirrer.

III. Suspension was passed through 40 # sieve and used for enteric coating.

2.3.3 Process of enteric coating of Experiment C4:

I. All the ingredients were weighed in required quantity.

II. Add EUDRAGIT® L30D-55 in 60% quantity of water under stirring.

III. Prepare 1N sodium hydroxide solution using part of remaining quantity of water.

IV. Add step III to step II slowly under stirring.

V. Add TEC & talc in remaining quantity of water and homogenize it for 30 minutes VI. Add step V to step IV under stirring and continue stirring for 20 minutes.

VII. Suspension was passed through 40 # sieve and used for enteric coating on intermediate coated pellets.

2.3.4 Process of enteric coating of Experiment C5:

I. All the ingredients were weighed in required quantity.

II. TEC and Talc were homogenized in water for 15 min then added slowly to the EUDRAGIT® L 30 D-55 dispersion while stirring, resulted suspension was mixed for 30 min using overhead stirrer.

III. Suspension was passed through 40 # sieve and used for enteric coating on intermediate coated pellets.

TABLE 21(a)

General Process Parameters for enteric coating of comparative experiment C1 & C2:

| General Process Parameters for enteric coating | | Experiment C1-C2 |
|---|---|---|
| Equipment used | | Neocota |
| Equipment setup | | |
| Silicone tube inner diameter | mm | 3.0 |
| Pan size | inch | 14 |
| Number of baffles | No.s | 6 |
| Process data | | |
| Pan RPM | RPM | 6-14 |
| Inlet temperature | ° C. | 55-65 |
| Product temperature | ° C. | 28-32 |
| Atomization pressure | bar | 1.5 |
| Spray rate | g/min | 1-8 |

TABLE 21(b)

General Process Parameters for enteric coating of comparative experiment C3 & C4:

| General Process Parameters in GPCG 1.1, bottom spray for enteric coating | | Experiment C3 | Experiment C4 | Experiment C5 |
|---|---|---|---|---|
| Equipment setup | | | | |
| Silicone tube inner diameter | mm | 3.0 | 3.0 | 3.0 |
| Air distribution plate | — | B | B | B |
| Column height | mm | 15 | 15 | 15-20 |
| Nozzle bore | mm | 0.8 | 0.8 | 0.8 |
| Process parameter setup | | | | |
| Filter shaking mode | — | Asynchronous | Asynchronous | Asynchronous |
| Filter shaking | sec | 5 | 5 | 5 |
| Filter shaking pause | sec | 250 | 100 | 250 |
| Air flow mode | — | Auto | Auto | Auto |
| Process data | | | | |
| Air flow | CFM | 40-70 | 63-76 | 70-80 |
| Atomization pressure | bar | 1.0-1.4 | 1.5 | 1.0 |
| Inlet temperature | ° C. | 35-39 | 52-55 | 38-41 |
| Product temperature | ° C. | 29-32 | 39-44 | 29-31 |
| Spray rate | g/min | 3-8 | 1-7 | 3-9 |

G. Analysis of enteric coated tablets/pellets:

ANALYTICAL METHODOLOGY

1. Sotalol Tablets: Refer analytical methodology of step D(2).

2. Pantoprazole Pellets:

A) Dissolution Conditions

1) Dissolution Parameters

Apparatus: USP Type II

Dissolution Medium: Acid stage medium for 2 hrs. followed by buffer stage medium (1 hr)

Volume of Medium: 1000 mL for acid stage, 1000 mL for buffer stage

Speed 50 rpm

Temperature 37° C.±0.5° C.

Withdrawal Volume 10 ml

Sample Dilution Dilute 10 mL of Aliquot with 2 mL of 0.5 N Sodium

Hydroxide Solution immediately.

2) Dissolution Mediums

I. Acid stage medium—0.1 N HCl; Buffer stage medium—pH 5.5 buffer

II. Acid stage medium—0.1 N HCl; Buffer stage medium—pH 4.5 buffer

3) Composition of Dissolution Mediums

1) Buffer pH 5.5—

1 g of Potassium dihydrogen phosphate, 2 g of Dipotassium hydrogen phosphate and 8.5 g of Sodium chloride was weighed and transferred to 1-liter beaker. To this, 500 mL water was added, salts were dissolved, and volume was made up to 1000 mL with water. The pH was adjusted to 5.5 (±0.05) using ortho-phosphoric acid.

2) Buffer pH 4.5—

Accurately weigh and transfer 2.99 g of Sodium acetate trihydrate to 1-liter beaker. To this add water to dissolve and make up volume to 1000 mL. Adjust the pH to 4.5 (±0.05) using glacial acetic acid.

3) Buffer pH 3.0—
Accurately weigh and transfer 8.98 gram of citric acid anhydrous and 2.13 gram of Tri-sodium citrate dihydrate in 1000 ml of water. Sonicate to dissolve. Adjust it to pH 3.5 (±0.05) using dilute NaOH.

4) Dissolution Procedure:

Acid Stage: Accurately weighed pellets of Pantoprazole were transferred in different dissolution jars and then the dissolution test was performed as per parameters given in the method above (Acid Stage). After 2 hours 10 mL of aliquot was removed, filtered through 0.45 μm PVDF membrane syringe filter. 1 mL was immediately diluted with 1 mL of 0.5 N sodium hydroxide solution and analyzed as acid stage sample solution.

Buffer Stage: The pellets after acid stage were transferred to buffer stage medium. The dissolution test was continued as per parameters given in the method above (Buffer Stage). The aliquots of each interval ware filtered through 0.45 μm PVDF membrane syringe filter discarding first few mL of the filtrate. 1 mL was immediately diluted with 1 mL of 0.5 N sodium hydroxide solution and analyzed as buffer stage sample solution.

B) Chromatographic Conditions

Chromatographic Conditions

Column: Agilent Zorbax XDB Eclipse C8 column, 150×4.6 mm, 5 μm

Mobile Phase: Water: Acetonitrile: Triethylamine (60:40:1) pH adjusted to 7.0 (+0.05) with orthophosphoric acid Wavelength: 290 nm Column Temp: 30° C.

Injection volume: 10 μL

Flow rate: 1.0 mL/minute

3. Benazepril Pellets:

A) Dissolution Conditions

1) Dissolution Parameters

Apparatus: USP Type II

Dissolution Medium: Acid stage medium for 2 hrs followed by buffer stage medium (1 hr)

Volume of Medium: 750 mL for acid stage, 1000 mL for buffer stage

Speed: 50 rpm

Temperature: 37° C.±0.5° C.

Withdrawal Volume: 10 ml

2) Dissolution mediums

I. Acid stage medium—0.1 N HCl; Buffer stage medium—pH 5.5 buffer

II. Acid stage medium—0.1 N HCl; Buffer stage medium—pH 4.5 buffer

III. Acid stage medium—0.1 N HCl; Buffer stage medium—pH 3.0 buffer

3) Composition of dissolution mediums

1) Buffer pH 5.5—

1 g of Potassium dihydrogen phosphate, 2 g of Di-potassium hydrogen phosphate and 8.5 g of Sodium chloride was weighed and transferred to 1 liter beaker. To this, 500 mL water was added, salts were dissolved and volume was made up to 1000 mL with water. The pH was adjusted to 5.5 (±0.05) using ortho-phosphoric acid 2) Buffer pH 4.5—

1 g of Potassium dihydrogen phosphate, 2 g of Di-potassium hydrogen phosphate and 8.5 g of Sodium chloride was weighed and transferred to 1 liter beaker. To this, 500 mL water was added, salts were dissolved, and volume was made up to 1000 mL with water. The pH was adjusted to 4.5 (±0.05) using ortho-phosphoric acid 3) Buffer pH 3.0—

1 g of Potassium dihydrogen phosphate, 2 g of Di-potassium hydrogen phosphate and 8.5 g of Sodium chloride was weighed and transferred to 1-liter beaker. To this, 500 mL water was added, salts were dissolved, and volume was made up to 1000 mL with water. The pH was adjusted to 3.0 (±0.05) using ortho-phosphoric acid 4) Dissolution Procedure:

Acid Stage: Accurately weighed pellets of Benazepril hydrochloride were transferred in different dissolution jars and then the dissolution test was performed as per parameters given in the method above (Acid Stage). After 2 hours 10 mL of aliquot was removed and analysed as acid stage sample solution.

Buffer Stage: The pellets after acid stage were transferred to buffer stage medium. The dissolution test was continued as per parameters given in the method above (Buffer Stage). The aliquots of each interval ware filtered through 0.45 μm nylon membrane syringe filter discarding first few mL of the filtrate and analysed as buffer stage sample solution.

B) Chromatographic Conditions

Column: Agilent Zorbax Eclipse XDB C18 column, 150×4.6 mm, 5 μm or equivalent

Mobile Phase: Buffer: MeOH (36:64)

Wavelength: 240 nm

Column Temp: 25° C.

Injection Volume: 20 μL

Flow rate: 1 mL/minute

Preparation of Buffer for Mobile Phase:

Accurately weighed 2.25 g of Tetra butyl ammonium bromide transferred in 500 mL water and dissolved. 0.55 mL of Glacial acetic acid added to it and volume was made up to 1000 mL with water. The buffer was filtered through 0.45 μm nylon membrane filter.

H. Summarization:

TABLE 22(a)

Performance of comparative experiment C1-C3:

| Experiment No. | C1 | C2 | C3 |
|---|---|---|---|
| Objective | Standard EUDRAGIT L30D-55 coating | "Duocoat Technology" according to WO2008/135090 A1 | Comparative example similar to example 1 of US 2005214371A1 using pantoprazole as API instead of lansoprazole |
| Core | ST | ST | PP |
| Inner layer (Seal coat) | ,, | .. | 1.7% w/w HPMC 6cps + Talc (146.25%) |
| Inner layer (Intermediate coat) | .. | 5 mg/cm² coating of EUDRAGIT L30D-55 Neutralized at pH6.0 with 20% Citric acid + TEC (5%) + Talc (50%) | 3.16% w/w HPMC 6 cps + Magnesium Carbonate (150%) |
| Outer layer (Enteric coat) | 5 mg/cm² coating of EUDRAGIT L30D-55 + TEC (10%) + Talc (50%) | 5 mg/cm² coating of EUDRAGIT L30D-55 + TEC (10%) + Talc (50%) | 20% w/w EUDRAGIT L30D-55 + TEC (9.5%) + Talc (42%) + TiO₂ (4.75%) |

TABLE 22(a)-continued

Performance of comparative experiment C1-C3:

| Experiment No. | C1 | C2 | C3 |
|---|---|---|---|
| Dissolution testing in acid media | | | |
| Enteric protection # | Pass | Pass | Pass! |
| Dissolution testing in buffer media of respective pH | | | |
| pH 5.5 | 4.4@ | 9.4@ | 26.29* |
| pH 5.8 | 8.2 | 83.5 | . . |
| pH 6.2@ | 85.5 | 93 | . |
| % alkali in alkali + enteric polymer** | NA | NA | 18% w/w |
| Inference | Very slow and incomplete release was observed at pH 5.8, 5.5 & below | Very slow and incomplete release was observed at pH 5.5 & below | Slow and incomplete drug release is obtained with comparative example similar to example 1 of US2005214371A1 using pantoprazole as API instead of lansoprazole |

\# Enteric protection after 2 hrs exposure to 0.1 N HCl;
$ Enteric protection after 1 hrs exposure to 0.1 N HCl;
\* Drug release after 45 mins;
@ Drug release after 30 mins
\*\* % alkali in alkali + enteric polymer =
Due to rapid degradation of Lansoprazole at lower pH conditions like pH 5.5, 4.5 and 3.0, Pantoprazole was used as API in example!
At enteric polymer build up 11.85% (Similar build up as US 2005214371 example 1), enteric protection for 2 hours was not obtained (degradation observed after 2 hr exposure to acid media—evaluated using back assay method) so further enteric coating done to get 20% enteric polymer build up which passed in enteric protection after 2 hour acid exposure.
Abbreviation:
ST: Sotalol Tablets;
HPMC: Hydroxy propyl methyl cellulose;
TEC: Triethyl Citrate;
TiO$_2$: Titanium Dioxide;
Qty.: Quantity;
gm: Grams

TABLE 22(b)

Performance of comparative experiment C4 & C5:

| Experiment No. | C4 | C5 |
|---|---|---|
| Objective | 30% Neutralized EUDRAGIT L30D-55 coating (according to US7932258B2) | Experiment with very low alkali concentration in inner layer keeping intermediate layer thickness constant |
| Core | BP | BP |
| Inner layer (Intermediate coat) | . . | 10% w/w HPMC + Glycerol (25%) + MgO (10%) |
| Outer layer (Enteric coat) | 15% w/w EUDRAGIT L 30D55 (30% neutralized with NaOH) + TEC (10%) + Talc (50%) | 20% w/w EUDRAGIT L30D-55 + TEC (10%) + Talc (50%) |
| Dissolution testing in acid media | | |
| Enteric protection # | Pass | Pass |
| Dissolution testing in buffer media of respective pH | | |
| pH 5.5* | 22.1 | 7.1 |
| pH 4.5* | | 6.8 |
| pH 3.0* | | 7.8 |
| % alkali in alkali + enteric polymer** | NA | 4.22% w/w** |
| Inference | Enteric resistance followed by slow and incomplete release in buffer pH 5.5 was observed | Use of 10% Magnesium oxide (w.r.t. dry binder quantity in intermediate coat) shows enteric resistance followed by less than 10% release in pH buffer 5.5 and lower pH |

\# Enteric protection after 2 hrs exposure to 0.1 N HCl;
\* Drug release after 45 mins;
\*\* % alkali in alkali + enteric polymer =
Abbreviation:
BP: Benazepril pellets;
TEC: Triethyl Citrate;
NA: Not applicable;
Qty.: Quantity;
gm: Grams

The invention claimed is:

1. A dosage form, comprising:
   a core, comprising a biologically active ingredient,
   an intermediate coating layer (ICL) onto the core, comprising an alkaline agent, wherein the alkaline agent is selected from the group consisting of calcium oxide, calcium carbonate, magnesium carbonate, magnesium oxide, sodium carbonate, sodium bicarbonate, sodium hydroxide, and a combination thereof, and
   an enteric coating layer (ECL) onto the intermediate coating layer, comprising an enteric polymer, the enteric layer forming an outer layer of the dosage form,
   wherein a relation of the alkaline agent to the enteric polymer is 5 to 95% when calculated by the formula:

$$\frac{\text{quantity of the alkaline agent in grams in the } ICL \times 100}{\text{(quantity of the alkaline agent in grams in the } ICL + \text{quantity of the enteric polymer in grams in the } ECL\text{)}}$$

wherein the biologically active ingredient is not a proton-pump inhibitor belonging to a class of substituted benzimidazole compounds,
   wherein the biologically active ingredient is released in an amount of 10% or less at a pH of 1.2 for 120 min, and in an amount of 50% or more at a pH from 3 to 5.5 for 45 min in the small intestine, and
   wherein the intermediate coating layer is present in an amount of 7.5 to 50% by weight, calculated based on the weight of the core,
   wherein the dosage form is suitable for the treatment of a disease requiring release of 50% or more of the biologically active ingredient.

2. The dosage form according to claim 1, wherein the disease and a class of the biologically active ingredient for treating the disease, respectively, are selected from the group consisting of gastrointestinal lavage and laxatives; an inflammatory bowel disease and corticosteroids; hypercholesterolemia or hypertriglyceridemia and statins; CHF and glycosides; arrhythmia and stereoisomers of quinidine; cancer and plant alkaloids; a bacterial infection and antibiotics; HIV and nucleosides; pancreatic insufficiency and lipases; major depressive disorder (MDD) or seasonal affective disorder (SAD) or an aid for smoking cessation and norepinephrine/dopamine-reuptake inhibitors (NDRI); pain or inflammation and NSAIDs; rheumatoid arthritis, osteoarthritis or ankylosing spondylitis and NSAIDs; Parkinson's disease and dopamine precursors; malaria and antimalarials; hypertension and beta-blockers; diabetes and biguanides; edema or chronic renal insufficiency and benzoic-sulfonamide-furans; mild to severe heart failure or left ventricular dysfunction after myocardial infarction with ventricular ejection fraction ≤40% hypertension and beta adrenoceptor blockers; a systemic fungal infection and antifungals; hyperlipoproteinemia or hypertriglyceridemia and fibrate antilipemics; heart failure and mineralocorticoid hormones; cancer and anthracycline antibiotics; hypertension, angina, or cluster headache prophylaxis and calcium channel blockers; and atrial fibrillation and beta blockers.

3. The dosage form according to claim 1, wherein the disease and the biologically active ingredient for treating the disease, respectively, are selected from the group consisting of gastrointestinal lavage and bisacodyl; an inflammatory bowel disease and budesonide; hypercholesterolemia or hypertriglyceridemia and fluvastatin; CHF and digoxin; arrhythmia and quinidine; cancer and etoposide; a bacterial infection and erythromycin, penicillin G, ampicillin, streptomycin, clarithromycin, or azithromycin; HIV and dideoxyinosine (ddI or didanosine), dideoxyadenosine (ddA), or dideoxycytosine (ddC); pancreatic insufficiency and a lipase; major depressive disorder (MDD) or seasonal affective disorder (SAD) or an aid for smoking cessation and bupropion; pain and inflammation, rheumatoid arthritis, osteoarthritis or ankylosing spondylitis and acetyl salicylic acid, diclofenac, or indomethacin; Parkinson's disease and levodopa; malaria and hydroxychloroquine sulphate; hypertension and atenolol; diabetes and metformin hydrochloride; edema or chronic renal insufficiency and benzoic-sulfonamide-furans; mild to severe heart failure or left ventricular dysfunction after myocardial infarction with ventricular ejection fraction ≤40% hypertension and furosemide; a systemic fungal infection and ketoconazole; hyperlipoproteinemia or hypertriglyceridemia and fenofibrate; heart failure and aldosteron; cancer and doxorubicin; hypertension, angina or cluster headache prophylaxis and verapamil; and atrial fibrillation and sotalol.

4. The dosage form according to claim 1, wherein the disease is atrial fibrillation and the biologically active ingredient is sotalol.

5. The dosage form according to claim 1, wherein the core comprises the biologically active ingredient distributed in a matrix structure or bound in a binder in a coating on an inner core.

6. The dosage form according to claim 1, wherein the alkaline agent is an alkali or an earth alkali metal salt.

7. The dosage form according to claim 1, wherein the alkaline agent is magnesium carbonate or magnesium oxide.

8. The dosage form according to claim 1, wherein the intermediate coating layer further comprises a plasticizer and/or a polymeric binder.

9. The dosage form according to claim 1, wherein the enteric polymer in the enteric coating layer is selected from the group consisting of an anionic (meth)acrylate copolymer, an anionic cellulose, an anionic polysaccharide, a polyvinyl acetate phthalate, and a mixture thereof.

10. The dosage form according to claim 9, wherein the enteric polymer comprises an anionic (meth)acrylate copolymer is selected from the group consisting of a copolymer comprising polymerized units of methacrylic acid and ethyl acrylate, a copolymer comprising polymerized units of methacrylic acid and methyl methacrylate, a copolymer comprising polymerized units of methacrylic acid, methyl acrylate, and methyl methacrylate, and a mixture thereof.

11. The dosage form according to claim 9, wherein the enteric polymer comprises an anionic cellulose is selected from the group consisting of carboxymethyl ethyl cellulose, a salt of carboxymethyl ethyl cellulose, cellulose acetate phthalate, cellulose acetate succinate, cellulose acetate trimellitate, hydroxypropyl methyl cellulose phthalate, hydroxypropyl methyl cellulose acetate succinate, and a mixture thereof.

12. The dosage form according to claim 1, wherein the enteric coating layer is present in an amount of 5 to 50% by weight, calculated based on a weight of the core and the intermediate coating layer.

13. The dosage form according to claim 1, wherein no other coating layer is between the intermediate coating layer and the core.

14. The dosage form according to claim 1, wherein no other coating layer is between the intermediate coating layer and the enteric coating layer.

15. The dosage form according to claim 10, wherein the enteric coating layer is an anionic (meth)acrylate copolymer selected from the group consisting of
   a) a (meth)acrylate copolymer comprising polymerized units of
      40 to 60% by weight of methacrylic acid; and
      60 to 40% by weight of ethyl acrylate;
   b) a (meth)acrylate copolymer comprising polymerized units of
      5 to 15% by weight of methacrylic acid;
      60 to 70% by weight of methyl acrylate; and
      20 to 30% by weight methyl methacrylate;
   c) a (meth)acrylate copolymer comprising polymerized units of
      40 to 60% by weight of methacrylic acid, and
      60 to 40% by weight of methyl methacrylate; and
   d) a (meth)acrylate copolymer comprising polymerized units of
      20 to 40% by weight of methacrylic acid; and
      60 to 80% by weight of methyl methacrylate.

* * * * *